United States Patent
Yodfat et al.

(10) Patent No.: US 7,572,290 B2
(45) Date of Patent: Aug. 11, 2009

(54) IMPLANTABLE INTRALUMINAL DEVICE AND METHOD OF USING SAME IN TREATING ANEURYSMS

(75) Inventors: Ofer Yodfat, Modi'in (IL); Baruch B. Lieber, North Miami Beach, FL (US); Ygael Grad, Tel-Aviv (IL); Boaz Nishri, Doar-Na Menashe (IL)

(73) Assignee: Surpass Medical Ltd., Tel-Aviv (IL)

( * ) Notice: Subject to any disclaimer, the term of this patent is extended or adjusted under 35 U.S.C. 154(b) by 0 days.

(21) Appl. No.: 11/907,675

(22) Filed: Oct. 16, 2007

(65) Prior Publication Data
US 2008/0039933 A1    Feb. 14, 2008

Related U.S. Application Data

(60) Division of application No. 10/910,621, filed on Aug. 4, 2004, now Pat. No. 7,306,624, which is a continuation-in-part of application No. 10/216,356, filed on Aug. 12, 2002, now abandoned, and a continuation-in-part of application No. PCT/IL01/00624, filed on Jul. 9, 2001.

(60) Provisional application No. 60/332,013, filed on Nov. 23, 2001.

(51) Int. Cl.
*A61F 2/06* (2006.01)
(52) U.S. Cl. .................... 623/1.39; 623/1.15
(58) Field of Classification Search ....... 623/1.51–1.54, 623/1.15–1.39
See application file for complete search history.

(56) References Cited

U.S. PATENT DOCUMENTS

| | | |
|---|---|---|
| 4,425,908 A | 1/1984 | Simon |
| 4,577,631 A | 3/1986 | Kreamer |
| 4,643,184 A | 2/1987 | Mobin-Uddin |
| 4,655,771 A | 4/1987 | Wallsten |
| 4,760,849 A | 8/1988 | Kropf |

(Continued)

FOREIGN PATENT DOCUMENTS

EP    0183372    6/1984

(Continued)

OTHER PUBLICATIONS

Barnett et al. "Causes and Severtity of Ischemic Stroke in Patients With Internal Carotid Artery Stenosis", JAMA, 283: 1429-1436, 2000.

(Continued)

*Primary Examiner*—Suzette J Gherbi (57) ABSTRACT

A method and apparatus for reducing blood flow to an aneurysm proximate to a bifurcation having a source blood vessel a first branch vessel and a second branch vessel, the method comprising: providing a first mesh-like tube of bio-compatible material, the first mesh-like tube exhibiting a porosity index pre-selected to skew blood flow about the bifurcation away from the aneurysm; inserting the first mesh-like tube into the source blood vessel and the first branch vessel; and securing the first mesh-like tube to at least one of the source blood vessel and the first branch vessel, whereby blood flowing from the source blood vessel flows without undue impedance to the first branch vessel and the second branch vessel while being skewed away from the aneurysm.

30 Claims, 5 Drawing Sheets

U.S. PATENT DOCUMENTS

| | | |
|---|---|---|
| 4,954,126 A | 9/1990 | Wallsten |
| 5,061,275 A | 10/1991 | Wallsten et al. |
| 5,324,304 A | 6/1994 | Rasmussen |
| 5,350,398 A | 9/1994 | Pavcnik et al. |
| 5,383,892 A | 1/1995 | Kowalewski et al. |
| 5,415,630 A | 5/1995 | Gory et al. |
| 5,443,497 A | 8/1995 | Venbrux |
| 5,456,712 A | 10/1995 | Maginot |
| 5,464,449 A | 11/1995 | Ryan et al. |
| 5,562,725 A | 10/1996 | Schmitt et al. |
| 5,769,816 A | 6/1998 | Barbut et al. |
| 5,807,330 A | 9/1998 | Teitelbaum |
| 5,843,089 A | 12/1998 | Sahatjian et al. |
| 5,843,172 A | 12/1998 | Yan |
| 5,855,599 A | 1/1999 | Wan |
| 5,876,367 A | 3/1999 | Kaganov et al. |
| 5,928,261 A | 7/1999 | Ruiz |
| 5,941,896 A | 8/1999 | Kerr |
| 5,951,599 A | 9/1999 | McCrory |
| 6,027,529 A | 2/2000 | Roychowdhury et al. |
| 6,030,414 A | 2/2000 | Taheri |
| 6,071,306 A * | 6/2000 | Angelini .................. 623/1.13 |
| 6,093,199 A | 7/2000 | Brown et al. |
| 6,146,370 A | 11/2000 | Barbut |
| 6,258,115 B1 | 7/2001 | Dubrul |
| 6,258,120 B1 | 7/2001 | McKenzie et al. |
| 6,261,305 B1 | 7/2001 | Marotta et al. |
| 6,312,463 B1 | 11/2001 | Rourke et al. |
| 6,348,063 B1 | 2/2002 | Yassour et al. |
| 6,383,171 B1 | 5/2002 | Gifford et al. |
| 6,409,750 B1 | 6/2002 | Hyodoh et al. |
| 6,409,757 B1 | 6/2002 | Trout, III et al. |
| 6,458,152 B1 | 10/2002 | Khosravi et al. |
| 6,475,208 B2 | 11/2002 | Mauch |
| 6,488,704 B1 * | 12/2002 | Connelly et al. ............ 623/1.15 |
| 6,499,487 B1 | 12/2002 | McKenzie et al. |
| 6,533,811 B1 | 3/2003 | Ryan et al. |
| 6,576,009 B2 | 6/2003 | Ryan et al. |
| 6,638,294 B1 | 10/2003 | Palmer |
| 6,673,089 B1 | 1/2004 | Yassour et al. |
| 6,740,112 B2 | 5/2004 | Yodfat et al. |
| 6,866,680 B2 | 3/2005 | Yassour et al. |
| 2003/0100945 A1 | 5/2003 | Yodfat et al. |
| 2003/0125801 A1 | 7/2003 | Yodfat et al. |
| 2004/0010307 A1 | 1/2004 | Grad et al. |
| 2004/0010308 A1 | 1/2004 | Zafrir-Pachter et al. |
| 2004/0024416 A1 | 2/2004 | Yodfat et al. |
| 2004/0167613 A1 | 8/2004 | Yodfat et al. |
| 2005/0010281 A1 | 1/2005 | Yodfat et al. |

FOREIGN PATENT DOCUMENTS

| | | |
|---|---|---|
| EP | 0880948 | 12/1998 |
| WO | WO 98/47447 | 10/1998 |
| WO | WO 98/58599 | 12/1998 |
| WO | WO 99/32050 | 7/1999 |
| WO | WO 00/53118 | 9/2000 |
| WO | WO 00/53119 | 9/2000 |
| WO | WO 02/055123 | 7/2002 |
| WO | WO 02/055125 | 7/2002 |
| WO | WO 03/043527 | 5/2003 |

OTHER PUBLICATIONS

Caplan "Multiple Potential Risks for Stroke", JAMA, 283(11): 1479-1480, 2000.

Hart et al. "Crystal Structure of An Endochitinase From Hordeum Vulgare L. Seeds", Journal of Molecular Biology, 229: 189-193, 1993.

Lanzino et al. "Efficacy and Current Limitations of Intravascular Stents for Intracranial Internal Carotid, Vertebral, and Basilar Artery Aneurysms", Journal of Neurosurgery, 91: 538-546, 1999.

Lieber et al. "Alteration of Hemodynamics in Aneurysm Models by Stenting: Influence of Stent Porosity", Annals of Biomedical Engineering, 25(3): 460-469, 1997. Abstract.

Marinkovic et al. "Anatomic and Clinical Correlations of the Lenticulostriate Arteries", Clinical Anatomy, 14: 190-195, 2001.

Petty "Ischemic Stroke Subtypes, A Population-Based Study of Incidence and Risk Factors", Stroke, p. 1513-1516, 1999.

Stroke Editorial Office "Major Ongoing Stroke Trials", p. 557-562, 2003.

Wakhloo et al. "Stents for Intracranial Aneurysms: The Beginning of A New Endovascular Era?", Neurosurgery, 43(2): 377-379, 1998.

Yu et al. "A Steady Flow Analysis on the Stented and Non-Stented Sidewall Aneurysm Models", Medical Engineering & Physics, 21(3): 133-141, 1999. Abstract.

* cited by examiner

IMPLANTABLE INTRALUMINAL DEVICE AND METHOD OF USING SAME IN TREATING ANEURYSMS

RELATED APPLICATIONS

This application is a divisional of U.S. patent application Ser. No. 10/910,621 filed Aug. 4, 2004, which is a continuation-in-part of U.S. patent application Ser. No. 10/216,356 filed Aug. 12, 2002, which a) claims the benefit of U.S. Provisional Patent Application No. 60/332,013 filed Nov. 23, 2001, and b) is also a continuation-in-part of PCT Patent Application No. PCT/IL01/00624 filed Jul. 9, 2001. The contents of all of the above applications are incorporated herein by reference.

FIELD OF THE INVENTION

The present invention relates to intraluminal devices implantable in a blood vessel for the treatment of aneurysms especially basal apex aneurysms. The invention also relates to methods of treating aneurysms using such intraluminal devices.

BACKGROUND OF THE INVENTION

A number of publications as listed at the end of this specification are incorporated herein by reference in their entireties for background information and are numerically referenced in the following text.

Intracranial aneurysms are the main cause of nontraumatic subarachnoid hemorrhage and are responsible for about 25% of all deaths relating to cerebrovascular events. Autopsy studies show that the overall frequency of intracranial aneurysms in the general population is approximately 5 percent and suggest that 10 to 15 million persons in the United States have or will have intracranial aneurysms [I]. In approximately 15,000 cases (6 cases per 100,000 persons per year), intracranial aneurysms rupture every year in North America [2]. Rupture of intracranial aneurysms leads to subarachnoid aneurysmal hemorrhage (SAH) which has a 30-day mortality rate of 45%, and results in approximately half the survivors sustaining irreversible brain damage [1, 2].

The primary goal of treatments for intracranial aneurysm is prevention of the rupture of the aneurysms, thereby preventing bleeding or rebleeding. At the present time, three general methods of treatment exist. These can be grouped according to their approach: extravascular, endovascular, and extra-endovascular.

The extravascular approach involves surgery or microsurgery of the aneurysm. One surgical procedure is to apply a metallic clip or a suture-ligation across the artery feeding the aneurysm (neck), thereby allowing the aneurysm to clot off and hopefully shrink. Another surgical procedure is to "surgically reconstruct" the aneurysmal portion of the artery, by surgically cut out the aneurysm and repairing the vessel by using a natural or synthetic vessel graft. Both of these surgical procedures typically require general anesthesia, craniotomy, brain retraction, and dissection of the arachnoid around the neck of the aneurysm.

Surgical treatment of vascular intracranial aneurysm is accompanied by a mortality rate of 3.8% and a morbidity rate of 10.9% [3]. Because of the high mortality and morbidity rates, and because the condition of many patients does not permit them to undergo an open operation, the surgical procedure is often delayed or not practical. For this reason the prior art has sought alternative means of treatment.

The development of microcatheters made possible the use of endovascular (catheter-based) procedures. The major advantage of the endovascular procedures is that they do not require the use of open surgery. They are generally more beneficial and have much lower mortality and morbidity rates than the extravascular procedures.

Many variations of endovascular procedures exist of which some of the more important are the following:

Placement of embolic material, such as metallic microcoils or spherical beads, inside the aneurysm sac in order to form a mass within this sac which will slow the blood flow and generally encourage the aneurysm to clot off and to shrink. To accomplish this procedure, a microcatheter is guided through the cerebral arteries until the site of the aneurysm is reached. The distal tip of the microcatheter is then placed within the sac of the aneurysm, and the embolic material is injected into the sac of the aneurysm. Typical microcatheters suitable for this procedure are disclosed in U.S. Pat. Nos. 5,853,418; 6,066,133; 6,165,198 and 6,168,592.

Widespread, long-term experience with this technique has shown several risks and limitations. The method has 4% morbidity and 1% mortality rate and achieves complete aneurysm occlusion in only 52% to 78% of the cases in which it is employed. The relatively low success rate is due to technical limitations (e.g., coil flexibility, shape, and dimensions) which prevent tight packing of the sac of the aneurysm, especially aneurysms with wide necks [3]. Other difficulties are associated with the presence of preexisting thrombus within the aneurysm cavity, which may be sheared off into the parent trunk leading to parent artery occlusion. Also aneurysm perforation may occur during placement of coils into the aneurysm. Additionally, occurrence of coil movement and compaction may foster aneurysm revascularization or growth.

2. Another endovascular technique for treating aneurysms involves inserting a detachable balloon into the sac of the aneurysm using a microcatheter. The detachable balloon is then inflated using embolic material, such as a liquid polymer material or microcoils. The balloon is then detached from the microcatheter and left within the sac of the aneurysm in an attempt to fill the sac and to form a thrombotic mass inside the aneurysm.

One of the disadvantages of this method is that detachable balloons, when inflated, typically do not conform to the interior configuration of the aneurysm sac. Instead, the aneurysm sac is forced to conform to the exterior surface of the detachable balloon. Thus, there is an increased risk that the detachable balloon will rupture the sac of the aneurysm.

3. Stent technology has been applied to the intracranial vasculature. The use of this technology has been limited until recently by the lack of available stents and stent delivery systems capable of safe and effective navigation through the intercranial vessels. The use of such stents is particularly difficult with respect to aneurysms in head blood vessels because of the number of perforating vessels in such blood vessels, and thereby the increased danger that one or more perforating vessels may be in the vicinity of such an aneurysm. The same is true with respect to bifurcations of a blood vessel splitting into one or more branch vessels, which may also be in the vicinity of an aneurysm. Where the blood supply to an aneurysm is to be reduced, it is critical that the blood supply to such perforating vessel or branch vessels, in the vicinity of the aneurysm not be unduly reduced to the degree causing damage to the tissues supplied with blood by such perforating or branch vessels.

Thus, there is a serious danger that the placement of a conventional endovascular stent within the parent artery across the aneurysm neck to reduce blood flow to the aneurysm, to promote intra-aneurysm stasis and thrombosis [4,5].

Stents having portions of different permeabilities are disclosed, for example, in McCrory U.S. Pat. No. 5,951,599, Brown et al U.S. Pat. No. 6,093,199, Wallsten U.S. Pat. No. 4,954,126, and Dubrul U.S. Pat. No. 6,258,115.

The McCrory patent discloses a braided stent having a first portion with a relatively high porosity index so as to be highly permeable to blood flow, and a second portion of lower porosity index so as to be less permeable to blood flow. When the stent is deployed, the portion of low permeability is located to overlie the neck of the aneurysm, and the portion of high permeability is spaced from the neck of the aneurysm. A braided stent construction with different porosities is also disclosed in the Dubrul patent.

Brown et al, on the other hand, discloses an intraluminal device or stent comprising a diverter, in the form of a low-permeability foam pad, to overlie the neck of the aneurysm, straddled on its opposite sides by a pair of high-permeability coil elements for anchoring the device in the blood vessel.

Figure 9:
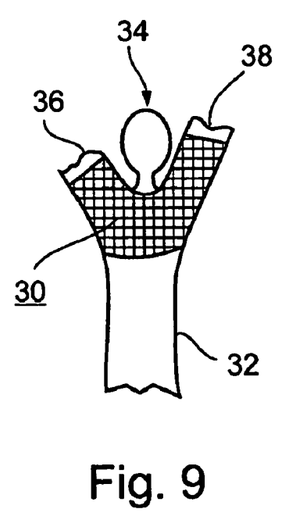

Wallsten U.S. Pat. No. 4,954,126, discloses a braided tube intraluminal device for use in various applications, one of which applications is to apply a graft to treat an aneurysm (FIG. 9). In this case, the complete braided tube would have high permeability with respect to blood flow therethrough since its function is to mount the grafts, but the graft would have low-permeability to decrease the possibility of rupture of the aneurysm.

Delivery devices for stents for use in the intracranial vasculature are well known at the art. Typical devices are disclosed, for example, in the following U.S. Pat. Nos. 5,496, 275; 5,676,659; and 6,254,628. The blood vessels in the brain are frequently as small as several millimeters, requiring that the catheters have an outside diameter as small as 2-8 French (0.66 mm to 2.64 mm).

Technically it is very difficult to produce and accurately deploy the stents described in the above McCrory, Brown et al and Wallsten patents for treating aneurysms by using presently available delivery systems. The difficulties include not only in producing such stents of different permeabilities, but also in deploying them such that the portion of low permeability is exactly aligned with the aneurysm neck. When the device is to be implanted in a blood vessel having an aneurysm at or proximate to a perforating vessel or a bifurcation leading to a branch vessel, the portion of high permeability must be precisely located at the perforating or branch vessels in order to maintain patency in the perforating or branch vessels. Additionally, particularly in tortuous, ectatic vessels, existing stiff stents are difficult to introduce and may results in kinking such as to cause the failure of the deployment process.

Furthermore, none of the prior art mentioned is suitable for use with a basal apex aneurysm.

For these reasons it is apparent that there is a need for a better intraluminal device to treat an aneurysm, particularly an intracranial aneurysm, and more particularly an intracranial aneurysm proximate to a bifurcation.

OBJECTS AND BRIEF SUMMARY OF THE INVENTION

An object of the present invention is to provide an intraluminal device having advantages in one or more of the above respects for implantation in a blood vessel having an aneurysm in order to treat the aneurysm. Another object of the invention is to provide such an intraluminal device particularly useful for implantation in a blood vessel having an aneurysms at or proximate to a bifurcation leading to a branch vessel such as to skew the blood flow away from the aneurysm while still maintaining patency in the perforating and/or branch vessels.

Another object of the invention is to provide an implantable intraluminal device for treating aneurysms in the intracranial vasculature that is sufficiently flexible and pliable so that it can be delivered easily to an intracranial site, deployed accurately, and then left in position to accomplish its purpose.

A further object of the invention is to provide a method of treating aneurysms by using intraluminal devices having the above features.

The present invention provides an intraluminal device implantable in the vicinity of a blood vessel bifurcation, the bifurcation having a source blood vessel a first branch vessel and a second branch vessel, an aneurysm being located proximate to the bifurcation, the device comprising: a mesh-like tube of bio-compatible material having an expanded condition in which the tube diameter is larger than the diameter of the blood vessel in which it is to be implanted, the mesh-like tube having a length sufficient to be anchored to both the source blood vessel and the first branch vessel thereby straddling the opening of the second branch vessel; the mesh-like tube also having a length such that, when placed and anchored to straddle the opening of the second branch vessel, it also straddles said aneurysm; the mesh-like tube being dimensioned and configured to have in its implanted condition a porosity index such as to skew the flow of blood away from the aneurysm sufficiently to decrease the possibility of rupture of the aneurysm but not to unduly reduce the blood flow to the second branch vessel to a degree likely to cause significant damage to tissues supplied with blood by such second branch vessel. The foregoing advantageous results have been found attainable when the mesh-like tube is designed to have, in its expanded condition, a porosity index of 60-75%; windows having an inscribed diameter of 30 -480 microns, preferably 50-320 microns; and/or a diameter of wire filaments of 10 -60 microns, preferably 20-40 microns; but when the filaments are of rectangular cross-section, a circumference 40-200 microns. The foregoing parameters are significantly different from stents that have heretofore been used.

Experimental evidence indicates that patency can be maintained and ischemia and infarction can be prevented if less than 50% of the ostial diameter is occluded [6].

In the described preferred embodiments, the windows in the mesh-like tube produce a porosity index of preferably 60%-75%. The porosity index (P.I.) is defined by the relation:

$$P.I. = 1 - \frac{S_m}{S_t}$$

wherein: "$S_m$" is the actual surface covered by the mesh-like tube, and "$S_t$" is the total surface area of the mesh-like tube. The porosity index of the existing typical stents is well above 80%. In the tube devices of the present invention, however, the porosity index is not more than 80%, preferably 55-80%, more preferably 60-75%.

In the described preferred embodiments, the mesh-like tube includes windows having an inscribed diameter of 30-480 µm, preferably 50-320 µm, in the implanted condition of the mesh-like tube.

According to the described preferred embodiments, the mesh-like tube includes a plurality of filaments of bio-compatible material extending helically in an interlaced manner in opposite directions so as to form a braided tube. It is contemplated, however, that other mesh-like structures could be used, such as woven or knitted tubes.

A maximum porosity index is attained when the braiding angle, in the implanted condition of the braided tube, is 90°. Decreasing the implanted braiding angle below 90° increases the radial force applied by the braided tube against the inner surface of the blood vessel and decreases the P.I. Increasing the implanted braiding angle above 90° decreases the radial force applied by the braided tube against the inner surface of the blood vessel and decreases the P.I. In cases, where low radial force is needed, the desirable P.I. can thus be achieved by increasing the implanted braiding angle, as described below with respect to specific examples. Preferably, the braided tube has a braiding angle in the range of 20%-150% in the implanted condition of the braided tube.

Also in the described preferred embodiments, the filaments, or at least most of them, are of circular cross-section and have a diameter of 10-50 μm, preferably 20-40 μm. The filaments could also be of non-circular cross-section, such as of square or rectangular cross-section, in which case it is preferred that they have a circumference of 40-200 μm. It is also possible to use combination of several filament diameters and filament materials in one device to achieve structural stability and/or desired radio-opacity characteristic. Preferably the braid is formed of 24-144 filaments, more preferably 62-120 filaments. The filaments may be of a suitable bio-compatible material, metal or plastic, and may include a drug or other biological coating or cladding.

According to another aspect of the present invention, there is provided an intraluminal device implantable in the vicinity of a blood vessel bifurcation, the bifurcation having a source blood vessel a first branch vessel and a second branch vessel, the aneurysm being located proximate to the bifurcation, the device comprising: a mesh-like tube of bio-compatible material having an expanded condition in which the tube diameter is slightly larger than the diameter of the blood vessel in which it is to be implanted, the mesh-like tube having a length sufficient to be anchored to both the source blood vessel and the first branch vessel thereby straddling the opening of the second branch vessel; the mesh-like tube also having a contracted condition wherein it is sufficiently flexible so as to be easily manipulatable through the blood vessel so as to be placed proximate to the bifurcation; the mesh-like tube being dimensioned and configured to have in its implanted condition a porosity index of 55-80% so as to skew the flow of blood away from the aneurysm sufficiently to decrease the possibility of rupture of the aneurysm but not to unduly reduce the blood flow to the second branch vessel to a degree likely to cause significant damage to tissues supplied with blood by such second branch vessel; wherein the mesh-like tube includes windows having an inscribed diameter of 30-480 μm in its implanted condition.

According to yet another aspect of the present invention, there is provided an intraluminal device implantable in the vicinity of a blood vessel bifurcation, the bifurcation having a source blood vessel a first branch vessel and a second branch vessel, the aneurysm being located proximate to the bifurcation, the device comprising: a mesh-like tube of bio-compatible material having an expanded condition in which the tube diameter is slightly larger than the diameter of the blood vessel in which it is to be implanted, said mesh-like tube having a length sufficient to be anchored to both the source blood vessel and the first branch vessel thereby straddling the opening of the second branch vessel; said mesh-like tube also having a contracted condition wherein it is sufficiently flexible so as to be easily manipulatable through the blood vessel so as to be placed proximate to the bifurcation; said mesh-like tube being dimensioned and configured to have in its implanted condition a porosity index of 55-80% so as to skew the flow of blood away from the aneurysm sufficiently to decrease the possibility of rupture of said aneurysm but not to unduly reduce the blood flow to said second branch vessel to a degree likely to cause significant damage to tissues supplied with blood by such second branch vessel; wherein said mesh-like tube is constituted of a plurality of filaments of bio-compatible material, in which at least most of said plurality of filaments are of circular cross-section having a diameter of 10-50 μm.

According to yet another aspect of the present invention, there is provided an intraluminal device implantable in the vicinity of a blood vessel bifurcation, the bifurcation having a source blood vessel a first branch vessel and a second branch vessel, the aneurysm being located proximate to the bifurcation, the device comprising: a mesh-like tube of bio-compatible material having an expanded condition in which the tube diameter is slightly larger than the diameter of the blood vessel in which it is to be implanted, the mesh-like tube having a length sufficient to be anchored to both the source blood vessel and the first branch vessel thereby straddling the opening of the second branch vessel; the mesh-like tube also having a contracted condition wherein it is sufficiently flexible so as to be easily manipulatable through the blood vessel so as to be placed proximate to the bifurcation; the mesh-like tube being dimensioned and configured to have in its implanted condition a porosity index of 55-80% so as to skew the flow of blood away from the aneurysm sufficiently to decrease the possibility of rupture of the aneurysm but not to unduly reduce the blood flow to the second branch vessel to a degree likely to cause significant damage to tissues supplied with blood by such second branch vessel; wherein the mesh-like tube is constituted of a plurality of filaments of bio-compatible material, in which at least most of the plurality of filaments are of rectangular cross-section having a circumference of 40-200 μm.

As will be described more particularly below, intraluminal devices constructed in accordance with the foregoing features show great promise in the treatment of aneurysms in general, and brain aneurysms in particular, since they are relatively easily manipulatable through the blood vessel to the implantation site, and when deployed in their expanded condition in the implantation site, they redirect/skew the flow of blood away from the aneurysm sufficiently to decrease the possibility of rupture thereof, while maintaining blood flow to the branch vessels in the vicinity of the aneurysm.

Further features and advantages of the invention will be apparent from the description below.

BRIEF DESCRIPTION OF THE DRAWINGS

The invention is herein described, by way of example only, with reference to the accompanying drawings, wherein.

It is to be understood that the drawings and the description below are provided primarily for purposes of facilitating understanding the conceptual aspects of the invention and various possible embodiments thereof, including what is presently considered to be preferred embodiments. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
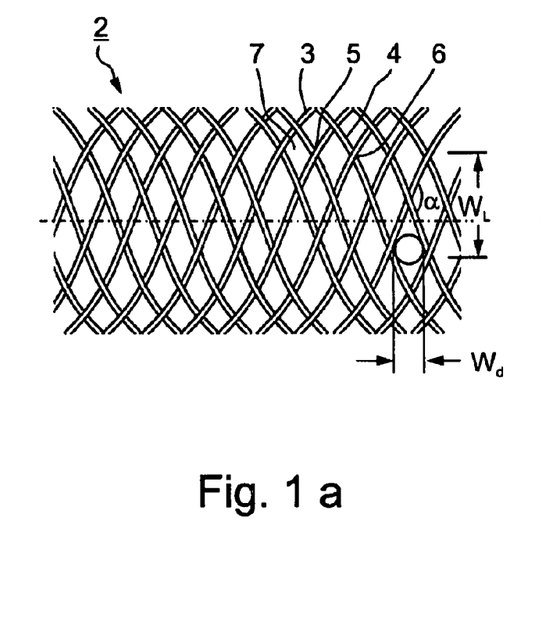
FIGS. 1a and 1b are side and end view, respectively, illustrating one form of intraluminal device constructed in accordance with the present invention, the device being shown in its implanted, expanded condition.
Figure 2:
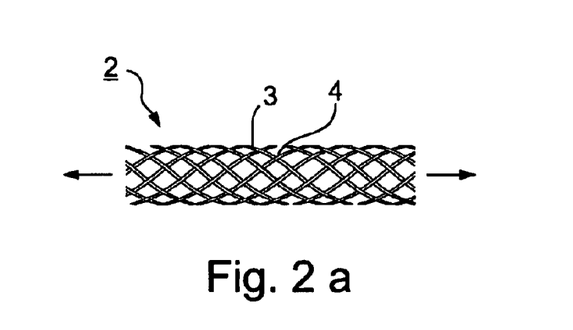
FIGS. 2a and 2b are corresponding views but illustrating the device in its contracted, stressed condition.

FIGS. 1a and 1b illustrate an intraluminal device, therein generally designated 2, constructed in accordance with the present invention in its implanted condition which it assumes in a blood vessel after deployment therein; whereas FIGS. 2a and 2b illustrate the intraluminal device 2 of FIGS. 1a and 1b in the contracted or stressed condition of the device which it assumes to facilitate its manipulation through the blood vessel to the deployment site.

As shown particularly in FIG. 1a, the intraluminal device includes a plurality of filaments of elastic or non-elastic biocompatible material, metal or plastic, extending helically in an interlaced manner to define a braided tube. Thus, shown in FIG. 1a are a first group of filaments 3 extending helically in one direction, and a second group of filaments 4 extending helically in the opposite direction, with the two groups of filaments being interwoven such that a filament 3 overlies a filament 4 at some points as shown at 5, and underlies a filament 4 at other points as shown at 6.

Filaments 3 and 4 thus define a braided tube having a plurality of windows 7. The inscribed diameter and the length of each window are shown at $W_d$ and $W_L$, respectively, in the implanted condition of the braided tube. These characteristics depend on, among other factors including: the number of filaments; the cross section of the filaments; and the implanted angle "α" at the cross-over points of the two groups of filaments 3, 4. It is understood by those skilled in the art that the above dimensions describe the dimensions in the implanted condition of the braided tube. The dimensions in the fully expanded unimplanted condition will be somewhat different, with the angle "α" and $W_L$ typically being larger than, and $W_d$ typically being smaller than, the equivalent respective dimensions in the implanted state.

Figure 3:
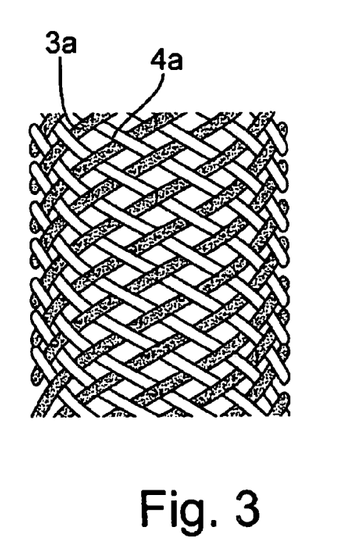
FIG. 3 more particularly illustrates the braid pattern of FIGS. 1a, 1b and 2a, 2b in the expanded condition of the braided tube.
Figure 4:
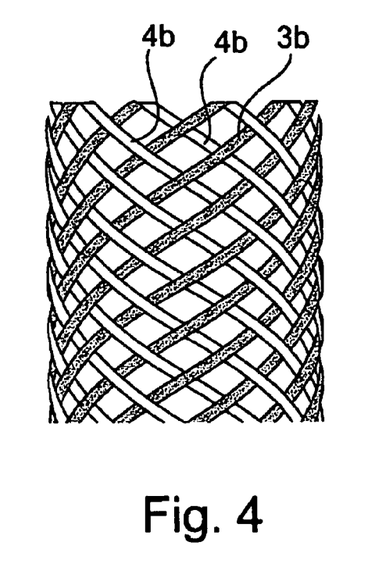
FIG. 4 illustrates another braid pattern, wherein one filament extending in one helical direction is interwoven over and under two filaments extending in the opposite helical direction.
Figure 5:
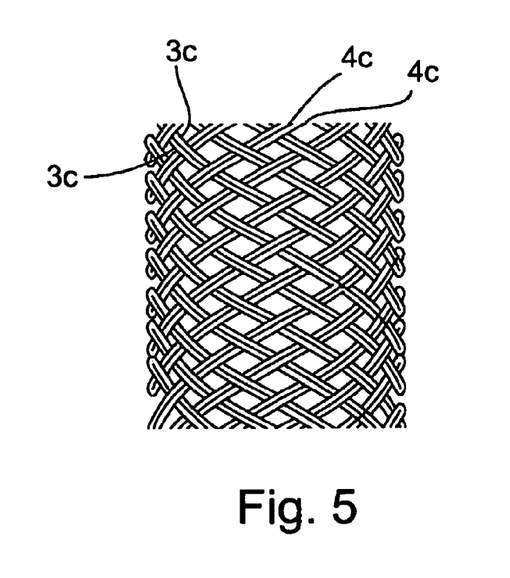
FIG. 5 illustrates a further braid pattern in which two (or more) contiguous filaments extending helically in one direction are interwoven over and under two (or more) contiguous filaments extending in the opposite direction.

FIG. 3 more particularly illustrates the above-described braid pattern in the fully expanded condition of the braided tube. Thus, as shown in FIG. 3, each filament 3a extending helically in one direction is interwoven with one filament 4a extending helically in the opposite direction. Such a braid pattern is sometimes called a "one over one" pattern. FIG. 4 illustrates a "one over two" pattern, in which each filament 3b extending helically in one direction is interwoven with two filaments 4b extending helically in the opposite direction. FIG. 5 illustrates a further braid pattern that may be used, in which two (or more) contiguous filaments 3c extending helically in one direction are interwoven with two (or more) contiguous filaments 4c extending helically in the opposite direction.

The braid pattern illustrated in FIG. 3 is of highest flexibility, whereas that illustrated in FIG. 5 is of lower flexibility but of higher strength.

Such braided-tube intraluminal devices are well-known, for example as described in Wallsten et al, U.S. Pat. No. 5,061,275 and Wallsten U.S. Pat. No. 4,954,126, the contents of which are incorporated herein by reference. They are generally used as stents for providing support to a wall of a blood vessel, for implanting a graft, e.g., to treat an aneurysm (FIG. 9 of the latter patent), or for other purposes. As known, the braided tube normally exhibits an expanded unimplanted condition having a diameter slightly larger than the diameter of the intended blood vessel in which it is to be implanted so that when the device is deployed it becomes firmly embedded in the wall of blood vessel. The braided tube is capable of being stressed into a contracted condition, as shown in FIGS. 2a and 2b, wherein the diameter of the braided tube is decreased, and its length increased, to permit manipulation of the braided tube through the blood vessel to the site of implantation.

Further information concerning the construction and deployment of such braided-tube intraluminal devices is available in the above-cited patents, and also in U.S. patent application Ser. No. 10/311,876 filed Dec. 20, 2002 entitled "IMPLANTABLE BRAIDED STROKE PREVENTING DEVICE AND METHOD OF MANUFACTURING" the contents of which are incorporated herein by reference.

When such braided tubes are used as stents within blood vessels, the filaments forming the braided tube are generally of a diameter exceeding 60 μm and define windows producing a porosity index significantly exceeding 80%. Such constructions, however, do not have the combination of flexibility to enable them to be easily manipulated through the tortuous blood vessels of the intracranial vascular system for preventing intracranial aneurysm ruptures, and the appropriate P.I. to enable them to skew the blood flow away form an aneurysm at or proximate to a bifurcation leading to a plurality of branch vessel.

These problems were sought to be overcome in the above-cited McCrory U.S. Pat. No. 5,951,599, Brown et al U.S. Pat. No. 6,093,199 and Wallsten U.S. Pat. No. 4,954,126, in producing braided tubes having a high-permeability portion to be deployed in the blood vessel and a low-permeability portion aligned with the aneurysm, but as indicated above such braided tubes constructions are difficult to produce, difficult to manipulate through the blood vessel, and difficult to accurately deploy at the site of the aneurysm.

According to the present invention, the constituent element making up the mesh-like tube are of a sufficiently small size in cross-section and define windows of a size such that the mesh-like tube, when in its contracted condition, is sufficiently flexible so as to be easily manipulatable through the blood vessel to be implanted at the bifurcation; and when in its implanted condition anchoring itself to both the source blood vessel and at least one of the branch vessels thereby skewing flow of blood away from the aneurysm sufficiently to decrease the possibility of rupture of the aneurysm. The skewing is caused by the flow of blood through the walls of the mesh-like tube, and the amount of skew is a function of the pre-determined implanted porosity index. In an exemplary embodiment, in which the mesh-like tube is constituted of braided filaments, the windows defined by the filaments of the braided tube are such as to reduce the flow of blood therethrough to the aneurysm to decrease the possibility of rupturing it, but not to unduly reduce the blood flow to the branch vessels to the degree likely to cause damage to tissues supplied with blood by such vessels. As indicated earlier, experimental evidence indicates that patency can be maintained, and ischemia and infarction can be prevented, if less than 50% of the ostial diameter of the branch vessel is occluded. The ostial diameter of intercranial branch vessels are typically on the order of 80-800 μm, thus to ensure patency of the intercranial branch vessels, filaments of the braided tube must be less than 50 μm in diameter for round filaments, and preferably less than or equal to 40 μm. For non-round filaments, a similar dimensional limitation is necessary.

Figure 6:
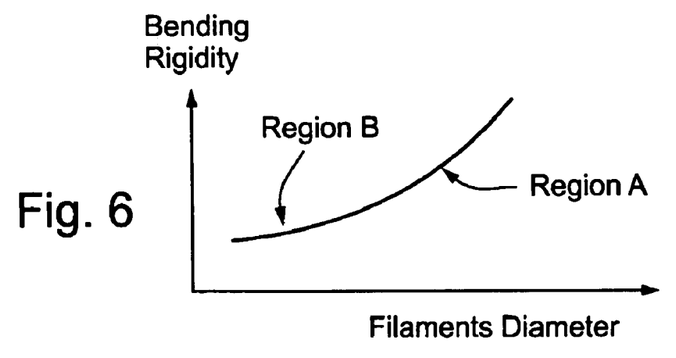
FIG. 6 schematically shows the relationship between the bending rigidity of the braided tube with respect to the diameter of the filaments producing the braided tube.

FIG. 6 schematically illustrates how the bending rigidity or flexibility of a braided tube varies with the diameter of the filaments. Region A in FIG. 6 illustrates typical diameters in conventional stents used for supporting blood vessels, which region usually starts above 60 μm and extends to several hundred μm. Region B in FIG. 6 illustrates the region of filament diameters for use in constructing braided tubes in accordance with the present invention. The filament diameters in this region would be significantly smaller than in region A, preferably being 10-50 μm, more preferably 20-40 μm.

The foregoing dimensions apply to the diameters of filaments of circular cross-section. Where the filaments are of non-circular cross-section, such as of rectangular or square cross-section, the filaments would preferably have a circumference of 40-200 μm. The circumference is defined in macro scale. The circumference can be enlarged at the micro-scale level by adding roughness to the wire, in order to control the neointimal growth and making the circumference in micro scale longer while keeping the macro scale the same. In this case the surface cross section of the filament would be in the range 75-3000 $\mu m^2$ preferably 300-1300 $\mu m^2$.

As indicated earlier, the windows formed in the braided tube would also be preferably within a predetermined range such as to skew the blood-flow away from the aneurysm, but maintain sufficient blood flow in the or branch vessels. Preferably the length of the window, i.e., its long dimension as shown at $W_L$ in FIG. 1a, would be within the range of 30-480 μm, more preferably 50-320 μm, in the implanted condition of the braided tube. Also, the implanted angle (α, FIG. 1a) would preferably be within the range of 20°-150°, more preferably 40-80° for high radial force and 100-140° for low radial force, in the implanted condition of the braided tube. In yet another preferred embodiment the braid angle in the implanted condition is approximately 90°, preferably in the range of 70°-110°.

The diameter and length of the braided tube in its normal, implanted condition, will vary according to the location and anatomical dimensions at the particular site of the implantation. Preferably, the windows are preferably globally (but not necessary locally) uniform in size such that any portion of the device can be placed across the opening of the branch vessel to skew the blood flow away from the aneurysm located proximate thereto, while the remaining portions of the device firmly contact the walls of the source blood vessel and at least one branch vessel thereby securely anchoring the device.

The filaments of the exemplary braided embodiment can be made of any suitable material which are bio-compatible and which can be worked into a braid. Bio-compatible herein includes any material that can be safely introduced and implanted in human or animal bodies for indefinite periods of time without causing any significant physiological damage. Preferably, the filaments are made of a material selected from among the 316L stainless steel, tantalum, and super elastic Nitinol, cobalt base alloy, polymer or any other suitable metal or metal combination. The filament can be coated with biocompatible coatings [Ulrich Sigwart, "Endoluminal Stenting", W. B. Saunders Company Ltd., London, 1996]. It is possible to use a combination of several filament materials in one device and combinations of several materials in one filament. The above embodiments have been described in relation to a braid mesh tube, however this is not meant to be limiting in any way. Other mesh-like structures, such as woven or knitted tubes exhibiting similar porosity and flexibility can be used without exceeding the scope of the invention.

In some situations, it may be desired to implant the device in a portion of a lumen, e.g., an artery, varying significantly in diameter along its length. As will be appreciated, if a constant diameter braided tube device is inserted into such a variable-diameter lumen, this may result in a defective anchoring of the device at the larger diameter portion of the lumen, and in a possible risk of the migration of the device within the lumen. This problem can be easily overcome in several ways, e.g., by creating braided devices with variable diameters along their longitudinal axis, or varying the pitch along the longitudinal axis, as described in the above-cited U.S. patent application Ser. No. 10/311,876 incorporated herein by reference.

Figure 7:
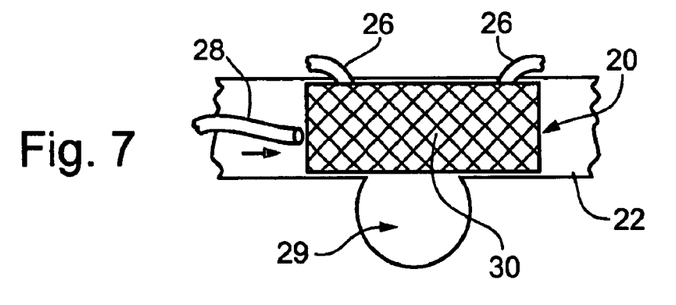
FIG. 7 schematically illustrates an intraluminal device implanted in a blood vessel having a plurality of perforating vessels in the vicinity of an aneurysm.

FIG. 7 diagrammatically illustrates the mesh-like tube device, therein generally designated 20, implanted in a blood vessel 22 having side wall aneurysm 29 in a region of a blood vessel 22 having a plurality of perforating vessels 26. Mesh-like tube device 20 is introduced, in its contracted condition, into blood vessel 22 and is manipulated to the implantation site by a microcatheter 28 where it is expanded such that it overlies neck 30 of aneurysm sac 29 and perforating vessels 26. Mesh-like tube 20 is thus firmly bonded, by its expansion to an implanted state, to the inner surfaces of blood vessel 22. As described above, braided tube device 20 is constructed such that, in its expanded implanted condition as shown in FIG. 4, it reduces the flow of blood to side wall aneurysm sac 29 sufficiently to decrease the possibility of rupture thereof, while at the same time, it does not unduly reduce the flow of blood to perforating vessels 26 to the degree likely to cause damage to the tissue supplied by perforating vessels 26. In a preferred embodiment the porosity index of braided tube device 20 overlying neck 30 of aneurysm sac 29 is between 55-80%, preferably 60-75%.

Figure 8:
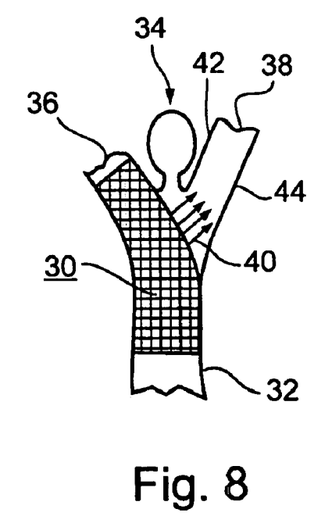
FIGS. 8, 9, 10, 11 and 12 illustrate various manners in which an intraluminal device constructed in accordance with the present invention may be implanted in a blood vessel having an aneurysm at or proximate to a bifurcation leading to one or more branch vessels.
Figure 10:
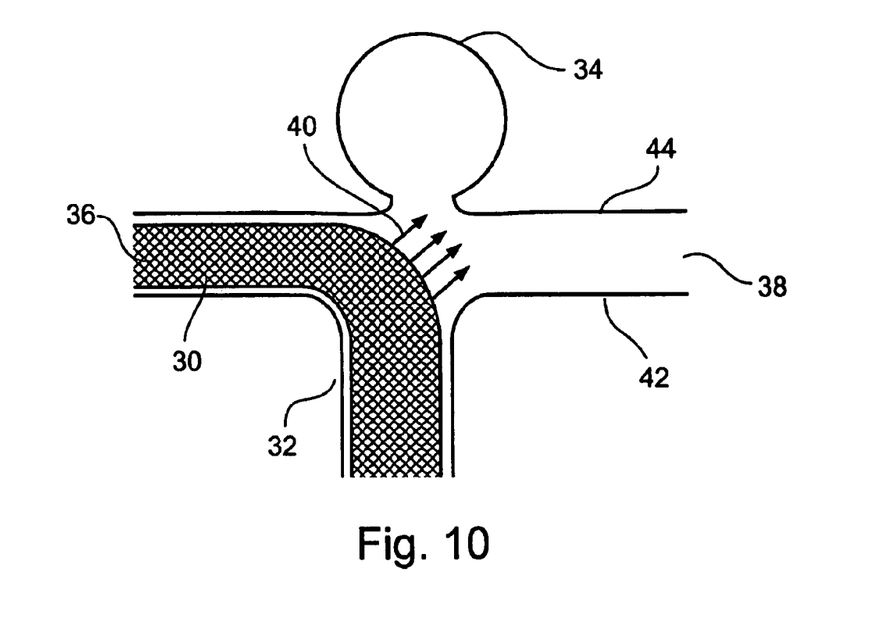

FIGS. 8, 9 and 10 illustrate the use of the braided tube device, generally designated 30, to treat an aneurysm in a blood vessel at or proximate to a bifurcation leading to two or more branch vessels.

Thus, FIG. 8 illustrates the braided tube device 30 implanted in a blood vessel 32 having an aneurysm 34 at the bifurcation leading to two branch vessels 36, 38. In the example illustrated in FIG. 8, the braided tube device 30 is deployed with one end embedded in the blood vessel 32 and the opposite end embedded within first branch vessel 36, so as to skew the blood flow away from the aneurysm sac 34, illustrated by flow lines 40 without unduly impeding blood flow to second branch vessel 38. As described earlier, however, while the reduced blood flow to the aneurysm sac 34 is sufficient to reduce the possibility of rupture of the sac, the reduced blood flow to second branch 38 is not sufficient so as to be likely to cause damage to the tissues supplied by that branch vessel. In an important aspect of the arrangement of FIG. 8, braided tube device 30 does not directly overly aneurysm sac 34. Flow lines 40 illustrate the blood flow exiting braided tube device 30 substantially bypassing aneurysm sac 34. Reducing the porosity index of braided tube device 30 increases the skew of blood flow from its normal path against inner wall 42 of second branch vessel 38, and redirects the flow towards outer wall 44 of second branch vessel 38. Further skewing of blood flow towards outer wall 44, thus bypassing aneurysm sac 34, is accomplished by increasing the pore density, defined as the number of pores per unit area. An increase in pore density is accomplished for the same porosity index by reducing the filament size, thus increasing the contact between blood particles and filaments. In a preferred embodiment, the porosity index is between 55-80%, preferably 60-75%.

FIG. 9 illustrates a variation wherein the opposite ends of the braided tube 30 are embedded in two branch vessels 36 and 38 at the bifurcation. In this case, the blood supply to the aneurysm sac 34 will also be reduced, and blood supply to both branch vessels 36, 38 will be reduced but not sufficient to cause damage to the tissues supplied by those branch vessels.

FIG. 10 illustrates an embodiment in which aneurysm sac 34 occupies the basal apex of bifurcation of blood vessel 32 into first branch vessel 36 and second branch vessel 38. Normal stenting of such a basal apex aneurysm sac is quite difficult, since the only approach to such an aneurysm in many cases is from blood vessel 32 or through the anterior vessels via the communication posterior arteries. This is particularly difficult in an intracranial embodiment, for which access must be accomplished through torturous blood vessels. Mesh-like tube device 30 is inserted through blood vessel 32 into first branch vessel 36, and expanded to its implanted state thus being securely embedded against the walls blood vessel 32 and first branch vessel 36. In a preferred embodiment mesh-like tube device 30 is of the self-expanding type. In an exemplary embodiment, mesh-like tube device 30 is a braided self-expanding type. In an important aspect of the arrangement of FIG. 10, mesh-like tube device 30 does not directly overly aneurysm sac 34.

In operation blood flow from source blood vessel 32 to branch vessel 36 is unimpeded. Blood flow from source blood vessel 32 to branch vessel 38 is reduced due to a P.I. of less than 100%, however not sufficient to cause damage to the tissues supplied by branch vessel 38. The P.I. is selected to skew the blood flow away from aneurysm sack 34 towards branch vessel 38 as shown by flow lines 40. The blood flow which normally would directly impact aneurysm sack 34 is redirected away from aneurysm sack 34 and vessel wall 44 of branch vessel 38, to flow towards vessel wall 42 of branch vessel 38.

Figure 11:
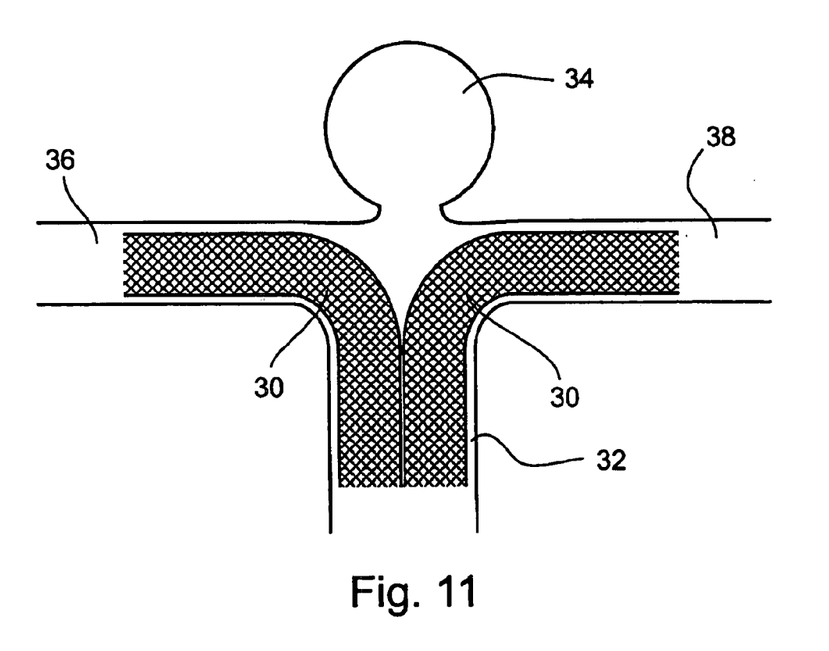

FIG. 11 shows another embodiment in which aneurysm sac 34 occupies the basal apex of bifurcation of source blood vessel 32 into first branch vessel 36 and second branch vessel 38. Two mesh-like tube devices 30 are inserted through blood vessel 32 into branch vessels 36 and 38, respectively and are expanded to their implanted state thus being securely embedded against the walls of source blood vessel 32, and branch vessels and 38, respectively. In a preferred embodiment both mesh-like tube devices 30 are of the self-expanding type. In an exemplary embodiment, mesh-like tube devices 30 are a braided self-expanding type. The P.I. is selected to skew the blood flow away from aneurysm sack 34. In an important aspect of the arrangement of FIG. 11, mesh-like tube devices 30 do not directly overly aneurysm sac 34.

Figure 12:
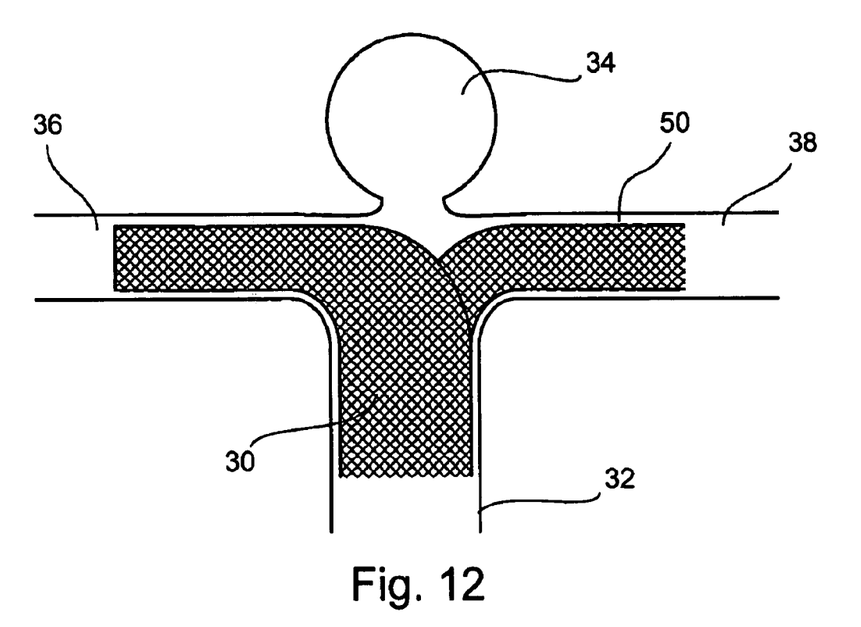

FIG. 12 shows another embodiment in which aneurysm sac 34 occupies the basal apex of bifurcation of blood vessel 32 into first branch vessel 36 and second branch vessel 38. A mesh-like tube device 30 is inserted through source blood vessel 32 into branch vessel 36 and expanded to its implanted state thereby being securely embedded against source blood vessel 32 and branch vessel 36. A mesh-like tube device 50 is inserted through mesh-like tube device 30 into branch vessel 38 and is expanded to its implanted state thus being securely embedded against the walls of source blood vessel 32 and branch vessel 38. In a preferred embodiment mesh-like tube devices 30 and 50 are of the self-expanding type. In an exemplary embodiment, mesh-like tube devices 30 and 50 are a braided self-expanding type.

Blood flow from source blood vessel 32 to first branch vessel 36 is unimpeded, and blood flow from source blood vessel 32 to second branch vessel 38 is unimpeded. Blood flow to aneurysm sac 34 is reduced by the skewing effect of mesh-like tube devices 30 and 50. In an important aspect of the arrangement of FIG. 12, mesh-like tube devices 30 and 50 do not directly overly aneurysm sac 34.

Analysis of a model similar to the setup illustrated in FIG. 8 was accomplished, in which the angle between the axis of branch blood vessel 38 and the axis of blood vessel 32 was approximately 30°, and the angle between the axis of branch blood vessel 38 and the wall of braided tube device 30 was approximately 55°. In the absence of braided tube device 30, representative of a PI of 100%, blood flow directly impacted the location of aneurysm 34 with a near 0° angle. Utilizing a braided tube device 30 exhibiting a PI of 85% skewed the blood flow near aneurysm 34 approximately 40° from the axis of blood vessel 32. Reducing the PI of braided tube device 30 to 74% increased the skew of the blood flow near aneurysm 34 to approximately 55° from the axis of blood vessel 32. Thus, a reduced PI successfully skewed the blood flow from directly impacting aneurysm 34.

While the invention has been described with respect to several preferred embodiments, it will be appreciated that these are set forth merely for purposes of example, and that many other variations, modifications and applications of the invention may be made. For example, the device could be composed of multiple tubular meshes, lying one above the other in layer-like formations. Also, the device could include a plurality of groups of filaments in the longitudinal and/or circumferential direction. Further, the invention could be implemented with respect to many of the other variations and applications described in the above-cited International Application PCT IL01/00624, equivalent to U.S. patent application Ser. No. 10/311,876 published as U.S. Patent Application 2004/0024416 incorporated herein by reference.

REFERENCES

1. An International Study of Unruptured Intracranial Aneurysms Investigators. N Engl J. Med. 1998 Dec. 10; 339 (24):1725-33: International study of unruptured intracranial aneurysms investigators; Unruptured intracranial aneurysms-risk of rupture and risks of surgical intervention.
2. Bederson J B, Awad I A, Wiebers D O, Piepgras D, Haley E C Jr, Brott T, Hademenos G, Chyatte D, Rosenwasser R, Caroselli C.; Recommendations for the management of patients with unruptured intracranial aneurysms: A Statement for healthcare professionals from the Stroke Council of the American Heart Association. Stroke. 2000 November; 31(11): 2742-50. No abstract available.
3. Wardlaw J M, White P M. The detection and management of unruptured intracranial aneurysms. Brain. 2000 February; 123 (Pt 2):205-21. Review.

4. Wakhloo A K, Lanzino G, Lieber B B, Hopkins L N. Stents for intracranial aneurysms: the beginning of a new endovascular era? Neurosurgery. 1998 August; 43(2):377-9.
5. Lieber B B, Stancampiano A P, Wakhloo A K. Alteration of hemodynamics in aneurysm models by stenting: influence of stent porosity. Ann Biomed Eng. 1997 May-June; 25(3): 460-9.
6. Lanzino G, Wakhloo A K, Fessler R D, Hartney M L, Guterman L R, Hopkins L N. Efficacy and current limitations of intravascular stents for intracranial internal carotid, vertebral, and basilar artery aneurysms. J. Neurosurg. 1999 October; 91(4):538-46.
7. Yu S C, Zhao J B. A steady flow analysis on the stented and non-stented sidewall aneurysm models. Med Eng Phys. 1999 April; 21(3):133-41.
8. Marinkovic S, Gibo H, Milisavljevic M, Cetkovic M. Anatomic and clinical correlations of the lenticulostriate arteries. Clin Anat. 2001 May; 14(3):190-5.

What is claimed is:

1. An intraluminal device implantable in the vicinity of a blood vessel bifurcation, the bifurcation having a source blood vessel, a first branch vessel, and a second branch vessel, an aneurysm being located proximate to the bifurcation, the device comprising:
   a mesh-like tube of bio-compatible material having an expanded condition in which the tube diameter is larger than the diameter of the blood vessel in which it is to be implanted, said mesh-like tube having a length sufficient to be anchored to both the source blood vessel and the first branch vessel thereby straddling the opening of the second branch vessel;
   said mesh-like tube also having a length such that, when placed and anchored to straddle the opening of the second branch vessel, it also straddles said aneurysm;
   said mesh-like tube being designed to have in its implanted condition a porosity index of 60-75% so as to skew the flow of blood away from the aneurysm sufficiently to decrease the possibility of rupture of said aneurysm but not to unduly reduce the blood flow to said second branch vessel to a degree likely to cause significant damage to tissues supplied with blood by such second branch vessel.

2. The intraluminal device according to claim 1, wherein said mesh-like tube includes windows having an inscribed diameter of 30-480 μm in its implanted condition.

3. The intraluminal device according to claim 1, wherein said mesh-like tube includes windows having an inscribed diameter of 50-320 μm in its implanted condition.

4. The intraluminal device according to claim 1, wherein said mesh-like tube is constituted of a plurality of filaments of bio-compatible material.

5. The intraluminal device according to claim 4, wherein at least most of said plurality of filaments are of circular cross-section having a diameter of 10-50 μm.

6. The intraluminal device according to claim 4, wherein at least most of said plurality of filaments are of circular cross-section having a diameter of 20-40 μm.

7. The intraluminal device according to claim 4, wherein at least most of said plurality of filaments are of rectangular cross-section having a circumference of 40-200 μm.

8. The intraluminal device according to claim 1, said mesh-like tube is formed of 24-144 filaments of bio-compatible material.

9. The intraluminal device according to claim 1, wherein said mesh-like tube is formed of 62-120 filaments of bio-compatible material.

10. The intraluminal device according to claim 1, wherein said mesh-like tube is constituted of a single tubular mesh.

11. The intraluminal device according to claim 1, wherein said mesh-like tube is constituted of multiple tubular meshes, lying one above the other in layer-like formations, in the implanted condition of the mesh-like tube.

12. An intraluminal device implantable in the vicinity of a blood vessel bifurcation, the bifurcation having a source blood vessel, a first branch vessel, and a second branch vessel, an aneurysm being located proximate to the bifurcation, the device comprising:
   a mesh-like tube of bio-compatible material having an expanded condition in which the tube diameter is larger than the diameter of the blood vessel in which it is to be implanted, said mesh-like tube having a length sufficient to be anchored to both the source blood vessel and the first branch vessel thereby straddling the opening of the second branch vessel;
   said mesh-like tube also having length such that, when placed and anchored to straddle the opening of the second branch vessel, it also straddles said aneurysm;
   said mesh-like tube being designed to have in its implanted condition a porosity index and windows having an inscribed diameter of 30-480 μm, such as to skew the flow of blood away from the aneurysm sufficiently to decrease the possibility of rupture of said aneurysm but not to unduly reduce the blood flow to said second branch vessel to a degree likely to cause significant damage to tissues supplied with blood by such second branch vessel.

13. The intraluminal device according to claim 12, wherein said mesh-like tube has a porosity index of 60-75% and includes windows having an inscribed diameter of 50-320 μm in its implanted condition.

14. The intraluminal device according to claim 12, wherein said mesh-like tube is constituted of a plurality of filaments of bio-compatible material.

15. The intraluminal device according to claim 14, wherein at least most of said plurality of filaments are of circular cross-section having a diameter of 10-60 μm.

16. The intraluminal device according to claim 14, wherein at least most of said plurality of filaments are of circular cross-section having a diameter of 20-40 μm.

17. The intraluminal device according to claim 14, wherein at least most of said plurality of filaments are of rectangular cross-section having a circumference of 40-200 μm.

18. The intraluminal device according to claim 12, said mesh-like tube is formed of 24-144 filaments of bio-compatible material.

19. The intraluminal device according to claim 12, wherein said mesh-like tube is a single tubular mesh.

20. The intraluminal device according to claim 12, wherein said mesh-like tube is constituted of multiple tubular meshes, lying one above the other in layer-like formations, in the implanted condition of the mesh-like tube.

21. An intraluminal device implantable in the vicinity of a blood vessel bifurcation, the bifurcation having a source blood vessel, a first branch vessel, and a second branch vessel an aneurysm being located proximate to the bifurcation, the device comprising:
   a mesh-like tube of bio-compatible material having an expanded condition in which the tube diameter is larger than the diameter of the blood vessel in which it is to be implanted, said mesh-like tube having a length sufficient to be anchored to both the source blood vessel and the first branch vessel thereby straddling the opening of the second branch vessel;

said mesh-like tube also having a length such that, when placed and anchored to straddle the opening of the second branch vessel, it also straddles said aneurysm;

said mesh-like tube being designed to have in its implanted condition a porosity index such as to skew the flow of blood away from the aneurysm sufficiently to decrease the possibility of rupture of said aneurysm but not to unduly reduce the blood flow to said second branch vessel to a degree likely to cause significant damage to tissues supplied with blood by such second branch vessel; said mesh-like tube being constituted of a plurality of filaments of bio-compatible material, in which at least most of said plurality of filaments are of circular cross-section having a diameter of 10-50 µm.

22. The intraluminal device according to claim 21, wherein said porosity index is 60-75%. and at least most of said plurality of filaments are of circular cross-section having a diameter of 20-40 µm.

23. The intraluminal device according to claim 21, said mesh-like tube is formed of 24-144 filaments of bio-compatible material.

24. The intraluminal device according to claim 21, wherein said mesh-like tube is single tubular mesh.

25. The intraluminal device according to claim 21, wherein said mesh-like tube is constituted of multiple tubular meshes, lying one above the other in layer-like formations, in the implanted condition of the mesh-like tube.

26. An intraluminal device implantable in the vicinity of a blood vessel bifurcation, the bifurcation having a source blood vessels a first branch vessels and a second branch vessel an aneurysm being located proximate to the bifurcation, the device comprising:

a mesh-like tube of bio-compatible material having an expanded condition in which the tube diameter is larger than the diameter of the blood vessel in which it is to be implanted, said mesh-like tube having a length sufficient to be anchored to both the source blood vessel and the first branch vessel thereby straddling the opening of the second branch vessel;

said mesh-like tube also having a length such that, when placed and anchored to straddle the opening of the second branch vessel, it also straddles said aneurysm;

said mesh-like tube being dimensioned and configured to have in its implanted condition a porosity index such as to skew the flow of blood away from the aneurysm sufficiently to decrease the possibility of rupture of said aneurysm but not to unduly reduce the blood flow to said second branch vessel to a degree likely to cause significant damage to tissues supplied with blood by such second branch vessel;

said mesh-like tube being constituted of a plurality of filaments of bio-compatible material, in which at least most of said plurality of filaments are of rectangular cross-section having a circumference of 40-200 µm.

27. The intraluminal device according to claim 26, wherein said mesh-like tube has a porosity index of 60-75%, and includes windows having an inscribed diameter of 30-480 µm in its implanted condition.

28. The intraluminal device according to claim 26, wherein said mesh-like tube includes windows having an inscribed diameter of 50-320 µm in its implanted condition.

29. The intraluminal device according to claim 26, said mesh-like tube is a single tubular mesh.

30. The intraluminal device according to claim 26, wherein said mesh-like tube is formed constituted of multiple tubular meshes, lying one above the other in layer-like formations, in the implanted condition of the mesh-like tube.

* * * * *